US009802025B2

(12) United States Patent
Khalaj

(10) Patent No.: US 9,802,025 B2
(45) Date of Patent: Oct. 31, 2017

(54) OVER-THE-NEEDLE EXPANDABLE CATHETER

(71) Applicant: Avent, Inc., Alpharetta, GA (US)

(72) Inventor: Steve Saeed Khalaj, Laguna Hills, CA (US)

(73) Assignee: Avent, Inc., Alpharetta, GA (US)

( * ) Notice: Subject to any disclaimer, the term of this patent is extended or adjusted under 35 U.S.C. 154(b) by 557 days.

(21) Appl. No.: 14/306,574

(22) Filed: Jun. 17, 2014

(65) Prior Publication Data

US 2015/0360004 A1 Dec. 17, 2015

(51) Int. Cl.
*A61M 25/00* (2006.01)
*A61M 25/06* (2006.01)
*A61B 5/00* (2006.01)
A61M 25/01 (2006.01)
A61N 1/05 (2006.01)

(52) U.S. Cl.
CPC ....... *A61M 25/0606* (2013.01); *A61B 5/4893* (2013.01); *A61B 5/6848* (2013.01); *A61M 25/0023* (2013.01); *A61M 25/005* (2013.01); *A61M 2025/0024* (2013.01); *A61M 2025/0175* (2013.01); *A61M 2205/0266* (2013.01); *A61N 1/0502* (2013.01); *A61N 1/0504* (2013.01); *A61N 1/0551* (2013.01)

(58) Field of Classification Search
CPC ............ A61M 5/3257; A61M 25/0606; A61M 25/0023; A61M 2025/0175; A61B 5/15119; A61B 5/6848; A61F 2210/0014; A61N 1/0502; A61N 1/0504
See application file for complete search history.

(56) References Cited

U.S. PATENT DOCUMENTS 4,969,890 A * 11/1990 Sugita ................ A61F 2/95
606/192
8,611,993 B2 12/2013 Vitullo et al.
2002/0142119 A1* 10/2002 Seward ................ A61L 29/126
428/36.9

(Continued)

FOREIGN PATENT DOCUMENTS

WO WO 00/04287 7/2000
WO WO 2009/091514 A2 7/2009

OTHER PUBLICATIONS

PCT Search Report, dated Sep. 10, 2015.

*Primary Examiner* — Nathan R Price
*Assistant Examiner* — Justin L Zamory
(74) *Attorney, Agent, or Firm* — Dority & Manning, P.A.

(57) ABSTRACT

The present disclosure is directed to an over-the-needle (OTN) catheter assembly having an expandable catheter. More specifically, the OTN catheter assembly includes a catheter having an expandable body with a proximal end and a distal end coaxially mounted onto a needle. The body defines a lumen extending from the proximal end to the distal end. Further, the body is expandable between a compressed length and an expanded length. The needle is configured within the lumen of the catheter and has a first length. The first length is longer than the compressed length of the catheter and shorter than the expanded length of the catheter. In addition, the body of the catheter is configured to expand from the compressed length to the expanded length when heat is applied to the catheter such that the distal end of the catheter extends past a distal end of the needle.

17 Claims, 4 Drawing Sheets

(56) References Cited

U.S. PATENT DOCUMENTS

| | | |
|---|---|---|
| 2004/0116896 A1 | 6/2004 | Massengale |
| 2004/0193109 A1* | 9/2004 | Prestidge ............. A61M 5/321 |
| | | 604/110 |
| 2014/0142509 A1 | 5/2014 | Bonutti et al. |

* cited by examiner

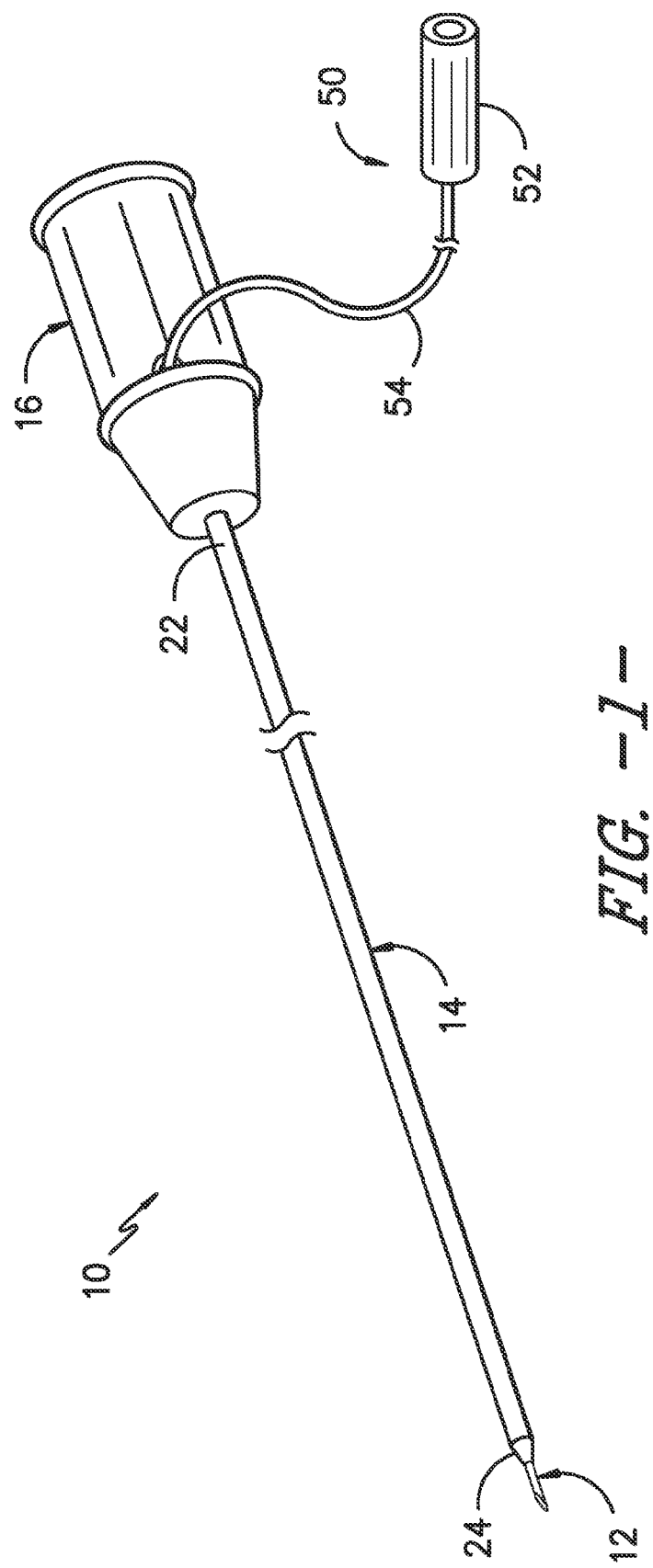
FIG. -1-

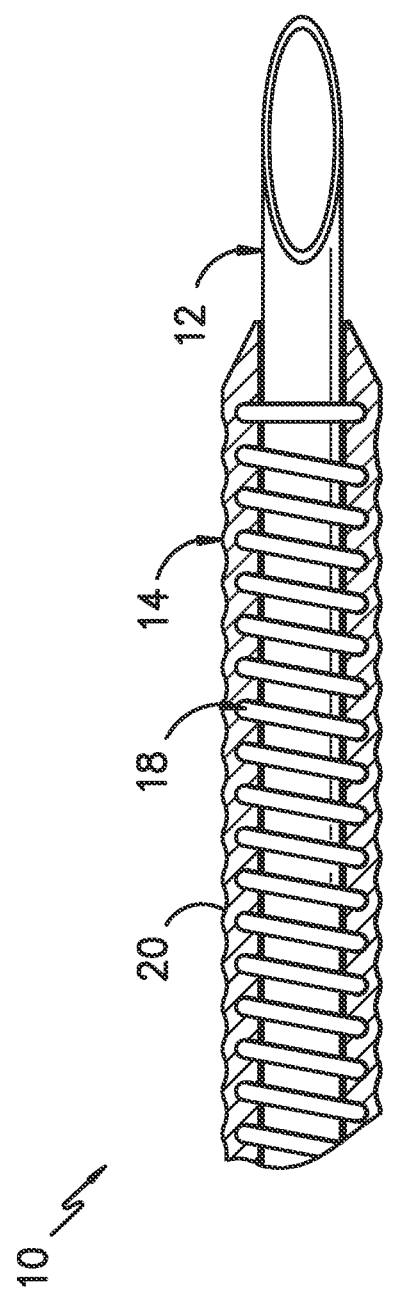
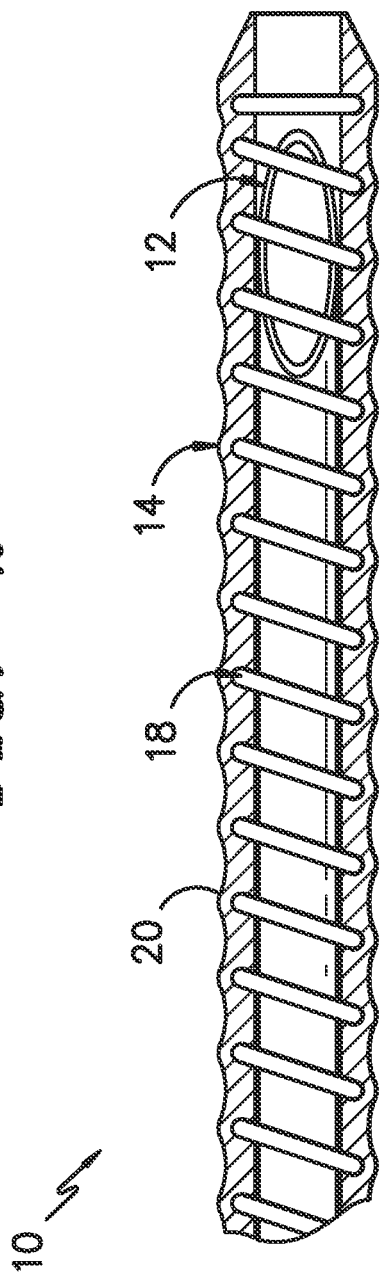
FIG. -2-
FIG. -3-

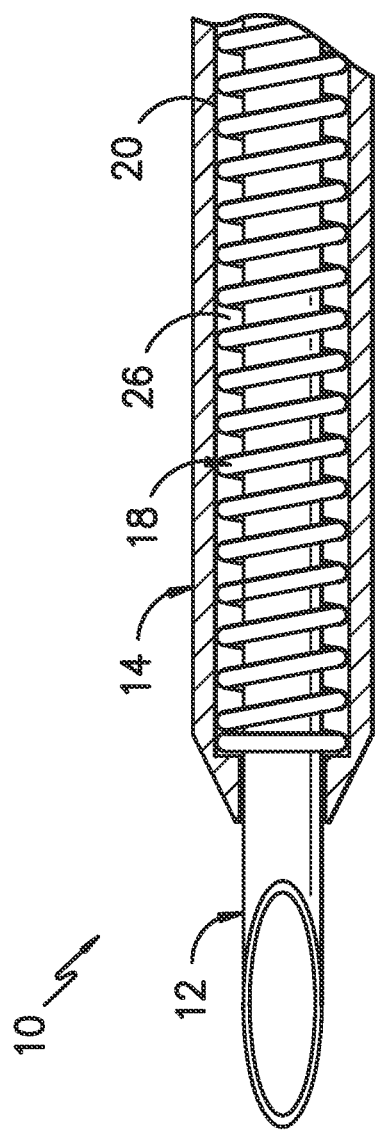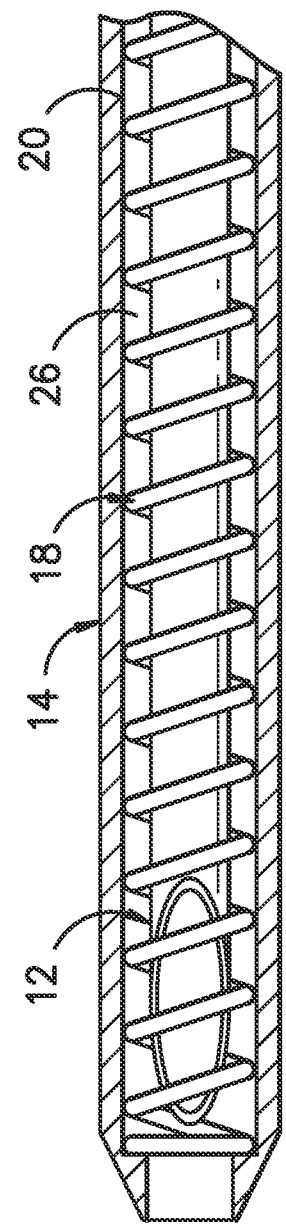

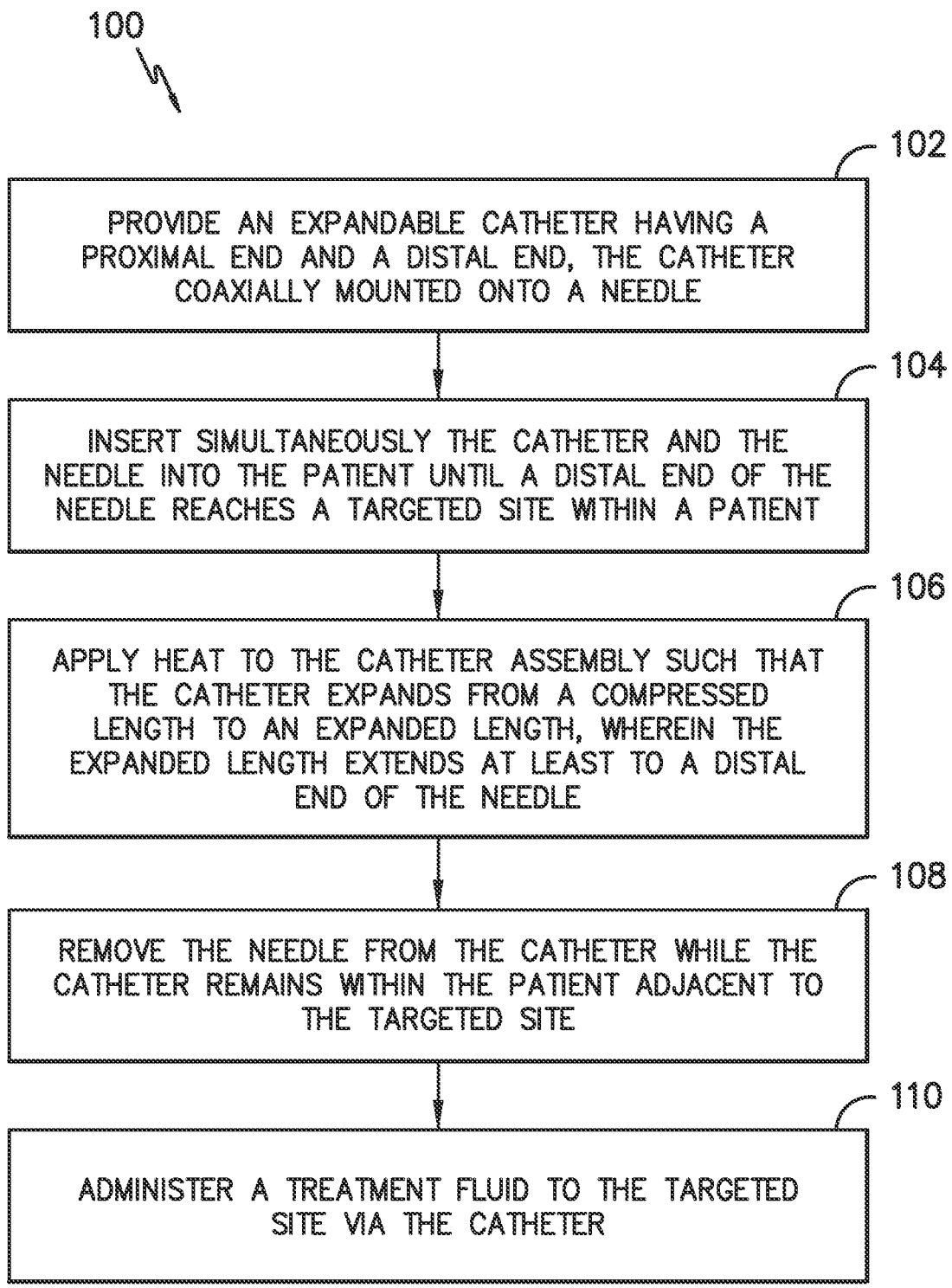
FIG. -6-

OVER-THE-NEEDLE EXPANDABLE CATHETER

FIELD OF THE INVENTION

The present invention relates generally to the field of medical catheters and more particularly to an over-the-needle (OTN) expandable catheter.

BACKGROUND

Devices used to administer a fluid inside the anatomy of a patient are well known. For example, hypodermic needles, catheters, and the like are often used to deliver medication and other fluids to targeted sites within the body. In many instances, catheters are preferred because they can deliver fluid to a particular site over a period of time. Since catheters are generally made of a flexible plastic material, a needle is typically used to insert the catheter within a patient. For example, certain catheters, generally referred to as "through-the-needle" catheters, often require stiff, hollow introducer needles for placement within the anatomy. Thus, the catheter can be inserted through the needle after the needle is located at the targeted site. Typically, such introducer needles have sharp tips that may damage tissue and/or nerves during their delivery into a body, thus causing discomfort for the patient.

Another type of catheters, generally referred to as "over-the-needle" (OTN) catheters, include a catheter coaxially mounted onto a needle. In this type of catheter, the catheter and the needle may be inserted into a patient together. Once the catheter and the needle are located at the targeted site, the needle can be removed, leaving the catheter in place. Thus, OTN catheters can be purposely directed to a targeted site within a patient without the need to thread the catheter therethrough. Accordingly, OTN catheters have gained increased attention in regard to delivering anesthetic medication, for example, for the purposes of nerve block.

A typical OTN catheter is shorter than its internal needle so as to not interfere with inserting the distal end of the needle into a patient. It is desirable, however, for the catheter to be the same length as the needle (or longer) such that the distal end of the catheter can be located more proximate to a nerve bundle for purposes of nerve block.

Accordingly, the present invention is directed to an expandable OTN catheter that addresses the aforementioned problems.

SUMMARY OF THE INVENTION

Objects and advantages of the invention will be set forth in part in the following description, or may be obvious from the description, or may be learned through practice of the invention.

In certain aspects, the present invention relates to an over-the-needle (OTN) catheter assembly having an expandable catheter. The assembly includes a catheter having an expandable body with a proximal end and a distal end coaxially mounted onto a needle. The body defines a lumen extending from the proximal end to the distal end. Further, the body is expandable between a compressed length and an expanded length. The needle is configured within the lumen of the catheter. The length of the needle is longer than the compressed length of the catheter, but shorter than the expanded length of the catheter. Thus, the body of the catheter is configured to expand from the compressed length to the expanded length when heat is applied to the catheter such that the distal end of the catheter expands past a distal end of the needle at or near a targeted site within the patient.

Accordingly, in one embodiment, the OTN catheter assembly includes a heat application assembly configured to apply heat to the catheter such that the body of the catheter expands from the compressed length to the expanded length. For example, in certain embodiments, the heat application assembly may include at least one of a nerve stimulation assembly, one or more battery devices, temperature-controlled water, an ultrasound device, a vibration device, or similar.

In another embodiment, at least a portion of the body of the expandable catheter includes a shape-memory material. For example, in certain embodiments, the shape-memory material may include at least one of a shape-memory polymer or a shape-memory alloy. More specifically, in one embodiment, the shape-memory polymer may include at least one of block copolymers, thermoplastic polymers, or thermosetting polymers. Alternatively, the shape-memory alloy may include Nitinol. In further embodiments, the shape-memory material may be shaped into a coil spring. More specifically, in certain embodiments, the coil spring may be embedded within a wall of the catheter. Thus, the catheter can expand and/or contract with the shape-memory material. Alternatively, the coil spring may be sized to fit within the lumen of the catheter. In such embodiments, the coil spring may be engaged with an inner wall of the catheter such that the catheter can expand and/or contract with the coil spring.

In another aspect, the present disclosure is directed to a method for using an over-the-needle (OTN) catheter assembly configured to provide treatment to a targeted site within a patient. The method includes a step of providing an expandable catheter having a proximal end and distal end that is coaxially mounted onto a needle. Another step includes inserting simultaneously the catheter and the needle into the patient until the distal end of the needle reaches the targeted site. The method also includes applying heat to the catheter assembly such that the catheter expands from a compressed length to an expanded length, wherein the expanded length extends at least to a distal end of the needle. A next step includes removing the needle from the catheter while the catheter remains within the patient adjacent to the targeted site. Thus, a further step includes administering a treatment fluid to the targeted site via the expanded catheter.

In one embodiment, the step of applying heat to the catheter assembly may further include at least one of the following: generating a current through the catheter via a nerve stimulation assembly, generating a current through the catheter via one or more battery devices, submerging at least a portion of the catheter into a temperature-controlled water, generating friction near the catheter, or generating vibration near the catheter via an ultrasound device. In addition, it should also be understood that the expandable catheter may include any or all of the features and/or embodiments as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an OTN catheter assembly in accordance with aspects of the invention;

FIG. 2 illustrates a detailed, side view of one embodiment of an OTN catheter assembly in a compressed state in accordance with aspects of the invention;

FIG. 3 illustrates a detailed, side view of one embodiment of an OTN catheter assembly in an expanded state in accordance with aspects of the invention;

FIG. 4 illustrates a detailed, side view of another embodiment of an OTN catheter assembly in a compressed state in accordance with aspects of the invention;

FIG. 5 illustrates a detailed, side view of another embodiment of an OTN catheter assembly in an expanded state in accordance with aspects of the invention; and FIG. 6 illustrates a flow diagram of one embodiment of a method for using an OTN catheter assembly to provide treatment to a targeted site within a patient in accordance with aspects of the invention.

DETAILED DESCRIPTION OF THE INVENTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The positional terms "proximal" and "distal" are used herein to orient the various components of the catheter assembly relative to each other and to the patient. "Distal" refers to the direction that is closest to the wound site (e.g., the distal end of the catheter is the end oriented towards a catheter insertion site), and "proximal" refers to the opposite direction (e.g., the proximal end of the catheter is typically inserted into a catheter connector, which in turn is typically connected to a fluid delivery device).

Generally, the present disclosure is directed to an over-the-needle (OTN) catheter assembly having an expandable catheter coaxially mounted onto a needle. More specifically, the catheter is configured to expand from a compressed length to an expanded length such that the catheter is shorter than the needle when inserted into a patient, but can be expanded past the needle after insertion in order to more accurately deliver a treatment fluid to a desired location within in the patient. Thus, the needle has a length that is longer than the compressed length of the catheter yet shorter than the expanded length of the catheter. In addition, the catheter is configured to expand from the compressed length to the expanded length when heat is applied to the catheter such that the distal end of the catheter expands past a distal end of the needle when the OTN catheter assembly is within a patient.

Referring now to the drawings, various views of one embodiment of an over-the-needle (OTN) catheter assembly 10 according to the present disclosure are illustrated in FIGS. 1-3. For example, as shown, the OTN catheter assembly 10 includes catheter 14 having a body 20 with a proximal end 22 and distal end 24 coaxially mounted onto a needle 12. Thus, the OTN catheter assembly 10 is configured such that the catheter and needle can be simultaneously inserted into a patient. In addition, the body 20 of the catheter 14 defines a lumen 26 extending from the proximal end 22 of the catheter 14 to the distal end 24. Thus, the catheter 14 is configured to deliver a treatment fluid to a targeted site within the patient via the lumen 26. More specifically, in certain embodiments, the proximal end 22 of the catheter 14 may include a hub 16 configured thereon for mating communication with a fluid delivery device (not shown) such that a treatment fluid can be delivered to a targeted site within a patient via the lumen 26 of the catheter 14. As mentioned, the fluid delivery device may be any suitable device known in the art, such as a pump, reservoir, syringe, or the like. Further, the hub 16 may have any conventional configuration, such as a Luer-lock fitting.

Referring particularly to FIGS. 2-5, at least a portion of the body 20 of the catheter 14 includes an expandable portion. More specifically, in certain embodiments, the expandable portion may be constructed of a shape-memory material. As used herein, a "shape-memory material" is generally defined as a light-weight material that has the ability to return from a deformed shape to its original shape when induced by an external trigger, such as a temperature change. Thus, in certain embodiments, shape-memory material essentially remembers its original shape such that when it is deformed, it is capable of returning to its pre-deformed shape when heated. It should be understood by those of ordinary skill in the art that the shape-memory material may include a shape-memory polymer, a shape-memory alloy, or similar. More specifically, in one embodiment, the shape-memory polymer may include at least one of block copolymers, thermoplastic polymers, thermosetting polymers, or similar. Alternatively, the shape-memory alloy may include nickel titanium, also known as Nitinol, which is a metal alloy of nickel and titanium.

In particular embodiments, the shape-memory material of the expandable portion of the catheter 14 may be constructed into a coil spring 18. For example, as shown, the coil spring 18 may be formed into the shape of a helix that can be easily compressed (FIGS. 2 and 4) and that can easily return to its natural length when unloaded or heated (FIGS. 3 and 5). Further, as shown in FIGS. 2 and 3, the coil spring 18 may be embedded within a wall of the catheter 14. Alternatively, as shown in FIGS. 4 and 5, the coil spring 18 may be sized to fit within the lumen 26 of the catheter 14. In such an embodiment, the shape-memory material (e.g. coil spring 18) is engaged with the flexible catheter 14 such that when the shape-memory material expands or contracts, the catheter 14 expands or contracts with the shape-memory material.

As mentioned, in certain embodiments, the expandable catheter 14 is configured to return to its original shape (i.e. its expanded length) when heated. Thus, the OTN catheter assembly 10 may include a heat application assembly 50 configured to apply heat to the catheter 14. For example, as shown in FIG. 1, the heat application assembly 50 may be coupled with the hub 16 of the catheter 14 so as to apply heat or current to the catheter 14. In further embodiments, the heat application assembly 50 may be directly coupled to the catheter 14 or the needle 12 or any other suitable component of the OTN catheter assembly 10. Further, as shown in FIG. 1, the heat application assembly 50 may correspond to a nerve stimulator apparatus having a nerve stimulator 52 that provides heat or current through one or more stimulator wires 54. Thus, when the stimulator wire 54 applies heat or current to the catheter 14, the distal end 24 of the catheter 14 expands at least to or past the distal end of the needle 12. It should be understood, however, that the heat application assembly 50 can further include any other suitable heating assembly known in the art and the illustrated embodiment is provided for illustrative purposes only. For example, in further embodiments, the heat application assembly 50 may also include one or more battery devices, temperature-controlled water, an ultrasound device, a vibration device, or similar.

Referring now to FIG. 6, a flow diagram of one embodiment of a method 100 for using an over-the-needle catheter assembly as described herein so as to provide treatment to a targeted site within a patient is illustrated. As shown in the illustrated embodiment, the method 100 includes a step 102 of providing an expandable catheter having a proximal end and a distal end that is coaxially mounted onto a needle. Another step 104 includes inserting simultaneously the catheter and the needle into the patient until the distal end of the needle reaches the targeted site. As mentioned, to reduce discomfort to the patient, it is desired for the catheter to be shorter than the needle during insertion of the catheter assembly into the patient at an insertion site. It would be beneficial, however, for the catheter to be longer than the needle (or the same length as the needle) after insertion to more accurately locate the catheter near a targeted site within the patient (e.g. adjacent to a nerve bundle). Thus, a further step 106 includes applying heat to the catheter assembly such that the catheter expands from a compressed length to an expanded length, wherein the expanded length expands at least to a distal end of the needle. As such, the OTN catheter assembly as described herein reduces insertion discomfort for the patient and is also capable of better targeting a treatment fluid (e.g. an anesthetic medication) to a targeted site within a patient, e.g. a nerve bundle. A next step 108 includes removing the needle from the catheter while the catheter remains within the patient adjacent to the targeted site. Thus, treatment fluid can then be administered to the targeted site within the patient via the catheter (step 110).

In one embodiment, the step 106 of applying heat to the catheter assembly may further include at least one of the following: generating a current through the catheter via a nerve stimulation assembly, generating a current through the catheter via one or more battery devices, submerging at least a portion of the catheter into temperature-controlled water, generating friction near the catheter, or generating vibration near the catheter via an ultrasound device. More specifically, in one embodiment, when current or heat is applied to or through the catheter, the catheter expands or returns to its original shape (i.e. at least to or past the distal end of the needle).

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. An over-the-needle catheter assembly, comprising:
a catheter comprising an expandable body having a proximal end and a distal end, said body defining a lumen extending from said proximal end to said distal end, said body comprising a coil spring constructed of a shape-memory material, said body expandable between a compressed length and an expanded length via said coil spring;
a needle configured within the lumen of the catheter, said needle comprising a first length, said first length being longer than said compressed length of said catheter and shorter than said expanded length of said catheter, wherein a distal end of said coil spring extends past a distal end of said needle when said body is expanded to said expanded length,
wherein said body of said catheter is configured to expand from said compressed length to said expanded length when heat is applied to said coil spring such that said distal end of said body of said catheter expands past said distal end of said needle.

2. The catheter assembly of claim 1, further comprising a heat application assembly configured to apply heat to said catheter such that said body of said catheter expands from said compressed length to said expanded length.

3. The catheter assembly of claim 2, wherein said heat application assembly comprises at least one of a nerve stimulation assembly, one or more battery devices, temperature-controlled water, an ultrasound device, or a vibration device.

4. The catheter assembly of claim 1, wherein said coil spring is embedded within a wall of said catheter.

5. The catheter assembly of claim 1, wherein said coil spring fits within said lumen of said catheter.

6. The catheter assembly of claim 1, wherein said shape-memory material comprises at least one of a shape-memory polymer or a shape-memory alloy.

7. The catheter assembly of claim 6, wherein said shape-member material comprises the shape-memory polymer, wherein said shape-memory polymer comprises at least one of block copolymers, thermoplastic polymers, or thermosetting polymers.

8. The catheter assembly of claim 6, wherein said shape-member material comprises the shape-memory alloy, wherein said shape-memory alloy comprises Nitinol.

9. A method for using an over-the-needle catheter assembly to provide treatment to a targeted site within a patient, the method comprising:
providing an expandable catheter having a proximal end and distal end, the catheter coaxially mounted onto a needle, said catheter comprising a coil spring constructed of a shape-memory material;
inserting simultaneously the catheter and the needle into the patient until the distal end of the needle reaches the targeted site;
applying heat to the coil spring of the catheter such that the catheter expands from a compressed length to an expanded length, wherein a distal end of said coil spring extends past the distal end of said needle when said catheter is expanded to said expanded length;
removing the needle from the catheter while the catheter remains within the patient adjacent to the targeted site; and
administering a treatment fluid to the targeted site via the catheter.

10. The method of claim 9, wherein applying heat to the coil spring of the catheter further comprises at least one of the following:
generating a current through the coil spring of the catheter via a nerve stimulation assembly, generating a current through the coil spring of catheter via one or more battery devices, submerging at least a portion of the coil spring of the catheter into a temperature-controlled water, generating friction near the coil spring of the catheter, or generating vibration near the coil spring of the catheter via an ultrasound device.

11. The method of claim 9, wherein at least a portion of the coil spring of the expandable catheter comprises a shape-memory material.

12. The method of claim 11, wherein said shape-memory material comprises a coil spring.

13. The method of claim 12, wherein said coil spring is embedded within a wall of said catheter.

14. The method of claim 12, wherein said coil spring is sized to fit within the lumen of the catheter.

15. The method of claim 11, wherein the shape-memory material comprises at least one of a shape-memory polymer or a shape-memory alloy.

16. The method of claim 15, wherein said shape-memory polymer comprises at least one of block copolymers, thermoplastic polymers, or thermosetting polymers.

17. The method of claim 15, wherein said shape-memory alloy comprises Nitinol.

* * * * *